(12) United States Patent
Song et al.

(10) Patent No.: US 12,148,070 B2
(45) Date of Patent: Nov. 19, 2024

(54) DEAD-TIME CORRECTION METHOD IN QUANTITATIVE POSITRON EMISSION TOMOGRAPHY (PET) RECONSTRUCTION FOR VARIOUS OBJECTS AND RADIOACTIVITY DISTRIBUTIONS

(71) Applicant: KONINKLIJKE PHILIPS N.V., Eindhoven (NL)

(72) Inventors: Xiyun Song, San Jose, CA (US); Jinghan Ye, Livermore, CA (US); Yanfei Mao, Highland Heights, OH (US); Chuanyong Bai, Solon, OH (US); Andriy Andreyev, Willoughby Hills, OH (US); Gregory Doughty, Beachwood, OH (US); Leonid Romanov, Mayfield Heights, OH (US); Zhiqiang Hu, Twinsburg, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1150 days.

(21) Appl. No.: 16/963,307

(22) PCT Filed: Jan. 24, 2019

(86) PCT No.: PCT/EP2019/051709
§ 371 (c)(1),
(2) Date: Jul. 20, 2020

(87) PCT Pub. No.: WO2019/145398
PCT Pub. Date: Aug. 1, 2019

(65) Prior Publication Data
US 2021/0366165 A1 Nov. 25, 2021

Related U.S. Application Data

(60) Provisional application No. 62/622,413, filed on Jan. 26, 2018.

(51) Int. Cl.
*G01T 1/161* (2006.01)
*A61B 5/00* (2006.01)
(Continued)

(52) U.S. Cl.
CPC ............ *G06T 11/005* (2013.01); *G01T 1/161* (2013.01); *G01T 1/164* (2013.01); *G01T 1/171* (2013.01); *A61B 5/00* (2013.01); *G01T 1/20* (2013.01)

(58) Field of Classification Search
CPC ............................ G06T 11/005; G01T 1/171
See application file for complete search history.

(56) References Cited

U.S. PATENT DOCUMENTS

| 7,180,074 B1 * | 2/2007 | Crosetto | G01T 1/1611 250/370.09 |
| 2006/0091314 A1 * | 5/2006 | Williams | G01T 1/1611 250/363.03 |

(Continued)

FOREIGN PATENT DOCUMENTS

| WO | WO-2016097977 A1 * | 6/2016 | ............. G01T 1/171 |
| WO | 2019057851 A1 | 3/2019 | |

OTHER PUBLICATIONS

International Search report and written opinion of PCT/EP2019/051709, dated Apr. 17, 2019.
(Continued)

*Primary Examiner* — Shefali D Goradia
*Assistant Examiner* — D J Dhooge

(57) ABSTRACT

An image reconstruction method includes: determining singles rates of radiation detectors in a frame of imaging data detected by the radiation detectors; determining an energy correction factor ($N_{wgt}$) for each radiation detector based on an energy spectrum distribution of gamma rays incident on the radiation detector during acquisition of the frame of imaging data; determining a singles live time correction factor for each radiation detector from the singles rate and the energy correction factor; determining a system coincidence live time correction factor from the system singles rate; for each line of response (LOR) connecting pairs of radiation detectors, determining a live time correction factor for the LOR from the determined singles live time correction factors of the pair of radiation detectors connected by the LOR and the determined system coincidence live time correction factor; and reconstructing the frame of imaging data using the determined LOR live time correction factors.

20 Claims, 5 Drawing Sheets

(51) Int. Cl.
   *G01T 1/164* (2006.01)
   *G01T 1/17* (2006.01)
   *G01T 1/20* (2006.01)
   *G06T 11/00* (2006.01)

(56) References Cited

U.S. PATENT DOCUMENTS

2011/0210255 A1* 9/2011 Kim .................. G01T 1/2985
                                                    250/362
2012/0070057 A1* 3/2012 Zhang ................ G06T 11/005
                                                    382/131
2014/0072194 A1* 3/2014 Hansis ................ G06T 11/005
                                                    382/128

OTHER PUBLICATIONS

Vicente, Esther et al, "Improved dead-time correction for PET scanners: application to small-animal PET", Physics in Medicine and Biology, Mar. 2013.
Yamamoto, Seiichi et al, "Deadtime correction method using random coincidence for PET", Journal of Nuclear Medicine, vol. 27, 1986, pp. 1925-1928.
Meikle, Steven R. et al "Quantitative Techniques in PET", Positron Emission Tomography, Jan. 2005.
Guerin, Bastein et al "Realistic PET Monte Carlo Simulation with Pixelated Block Detectors, Light Sharing, Random Coincidences and Dead-Time Modeling", IEEE Transactions on Nuclear Science, vol. 55, No. 3, Jun. 2008.
Daube-Witherspoon, Margaret et al "Unified Deadtime Correction Model for PET", IEEE Transactions on Medical Imaging, vol. 10, No. 3. Sep. 1991.

* cited by examiner

DEAD-TIME CORRECTION METHOD IN QUANTITATIVE POSITRON EMISSION TOMOGRAPHY (PET) RECONSTRUCTION FOR VARIOUS OBJECTS AND RADIOACTIVITY DISTRIBUTIONS

CROSS-REFERENCE TO PRIOR APPLICATIONS

This application is the U.S. National Phase application under 35 U.S.C. § 371 of International Application No. PCT/EP2019/051709, filed on Jan. 24, 2019, which claims the benefit of U.S. Provisional Patent Application No. 62/622,413, filed on Jan. 26, 2018. These applications are hereby incorporated by reference herein.

FIELD

The following relates generally to the medical imaging arts, emission imaging arts, positron emission tomography (PET) imaging arts, single photon emission computed tomography (SPECT) imaging arts, medical image interpretation arts, image reconstruction arts, and related arts.

BACKGROUND

Dead-time and pile-up are common issues of positron emission tomography (PET) imaging systems that cause nonlinear response to radioactivity in a field of view (FOV). Dead-time can be defined as the minimum amount of processing time to resolve two input signals as separate events. When a new valid event arrives while the detector is still busy processing a previous event, the new event can be missed, leading to losses in counts. In the situation of a pile-up, more than one incoming photon deposits energy in the same detector but are triggered as a single event, which is similar to dead-time losses, and cause the read-out energy to be higher than the actual energy. This causes a pile-up shift energy spectrum of incoming events. When the energy of an event is shifted from originally below the low threshold of energy window, such as scattered photons, to within the energy window, it causes gain in counts. When it shifts the energy of an event from within the energy window to above the high threshold of energy window, it causes loss in counts. The overall effects of the dead-time and pile-up can be looked as "effective" dead-time (See Esther Vicente, Joaquin Lopez Herraiz, et al, "Improved dead-time correction for PET scanners: application to small-animal PET", Physics in Medicine and Biology, March 2013). In general, the higher the activity, the higher fraction of losses in counts due to dead-time. It is also known that the overall dead-time loss fraction varies with object size, shape and radioactivity distribution (See Yamamoto S, Amano M, Miura S, et al, "Deadtime correction method using random coincidence for PET", J. Nucl. Med. 27 1925-8).

In order to achieve quantitative results, PET data should be corrected for the loss occurring due to dead-time.

Dead-time correction deployed in current PET systems is typically implemented during the image reconstruction phase. In short, such systems model the loss due to dead-time as a function of the total system average singles rate of all detectors, referred to as a system singles rate in order to differentiate from the singles rates of individual detectors. This approach is based on two assumptions: 1) all lines of response (LORs) experience the same amount (or fraction) of count loss due to dead-time; and 2) all PET imaging studies experience the same amount (or fraction) of count loss due to dead-time as long as the system singles rates are the same, regardless of the size, shape, or radioactivity distribution. More specifically, it takes the system singles rate that is averaged from the beginning and ending of an acquisition at one bed position, searches a scaling factor from the lookup table of dead-time correction factor vs system singles rate, and then equally applies this interpolated scaling factor to all events or all LORs for dead-time correction during a reconstruction. The lookup table is pre-generated from a calibration procedure using a cylinder phantom (e.g., 20 cm in diameter) filled with uniformly distributed radioactivity and placed at the center of FOV of the PET system. The lookup table is then used for all sequential studies, despite of variations in objects shape and radioactivity distributions, until replaced by a new calibration.

The above approach has some disadvantages. Because singles rates of individual detectors (or detector blocks) vary depending on activity and attenuation distributions of the object, losses due to dead-time also vary with each detector and LOR. The above approach neglects this difference and assumes all LORs share the same fraction of loss due to dead-time.

Furthermore, the dead-time calibration lookup table is generated using data from a specific uniform cylinder phantom placed at the center of FOV and then applied to all sequential studies of various patients/objects purely based on one parameter—system singles rate. In practice, for a different setup, for example, using a bigger phantom, a line source, a point source, or non-uniform patient distribution, the actual dead-time loss can be significantly different from that observed in the calibration study even if the system singles rates are the same. In general, the relationship between dead-time correction factor vs system singles rate described in the lookup table is valid for objects similar to this uniform cylinder phantom setup only. When applied to other setups, or for clinical patients, it can result in significant bias. In fact, this is a major degrading factor for the National Electrical Manufacturers Association (NEMA) Accuracy (relative count rate error) test, in which a line source is placed off-center in a cold cylinder background.

The following discloses new and improved systems and methods to overcome these problems.

SUMMARY

In one disclosed aspect, a non-transitory computer-readable medium stores instructions readable and executable by a workstation including at least one electronic processor to perform an image reconstruction method. The method includes: determining singles rates of a plurality of radiation detectors in a frame of imaging data detected by the radiation detectors; determining an energy correction factor ($N_{wgt}$) for each radiation detector based on an energy spectrum distribution of gamma rays incident on the radiation detector during acquisition of the frame of imaging data; determining a singles live time correction factor for each radiation detector from the singles rate and the energy correction factor determined for the radiation detector; for each line of response (LOR) of a plurality of LORs connecting pairs of radiation detectors, determining a live time correction factor for the LOR from the determined singles live time correction factors of the pair of radiation detectors connected by the LOR; and reconstructing the frame of imaging data using the determined LOR live time correction factors.

In another disclosed aspect, an image reconstruction method includes: determining singles rates of a plurality of radiation detectors in a frame of imaging data detected by the radiation detectors; determining an energy correction factor ($N_{wgt}$) for each radiation detector based on an energy spectrum distribution of gamma rays incident on the radiation detector during acquisition of the frame of imaging data; determining a low energy trigger correction factor (R) based on based on a ratio of the portion of the energy spectrum distribution of gamma rays incident on the radiation detector during acquisition of the frame of imaging data that fall in (i) an acquisition energy window (In-Ewindow) versus (ii) an extended energy window (Full-Ewindow) encompassing the acquisition energy window and a lower trigger energy window (Below-Ewindow); determining a singles live time correction factor for each radiation detector from the singles rate, the energy correction factor determined for the radiation detector, and the low energy trigger correction factor; for each line of response (LOR) of a plurality of LORs connecting pairs of radiation detectors, determining a live time correction factor for the LOR from the determined singles live time correction factors of the pair of radiation detectors connected by the LOR; reconstructing the frame of imaging data using the determined LOR live time correction factors; and at least one of displaying the reconstructed frame of imaging data and storing the reconstructed frame of imaging data.

In another disclosed aspect, an imaging system includes an image acquisition device comprising a plurality of radiation detectors. At least one electronic processor is programmed to: determine singles rates of a plurality of radiation detectors in a frame of imaging data detected by the radiation detectors; determine a low energy trigger correction factor (R) based on a ratio of the portion of the energy spectrum distribution of gamma rays incident on the radiation detector during acquisition of the frame of imaging data that fall in (i) an acquisition energy window (In-Ewindow) versus (ii) an extended energy window (Full-Ewindow) encompassing the acquisition energy window and a lower trigger energy window (Below-Ewindow); determine a singles live time correction factor for each radiation detector from the singles rate and the low energy trigger correction factor (R); for each line of response (LOR) of a plurality of LORs connecting pairs of radiation detectors, determine a live time correction factor for the LOR from the determined singles live time correction factors of the pair of radiation detectors connected by the LOR; and reconstruct the frame of imaging data using the determined LOR live time correction factors.

One advantage resides in providing an emission imaging system with improved dead time correction.

Another advantage resides in compensating for dead time variations between individual LORs and from imaging object to imaging object.

Another advantage resides in compensating for dead time loss bias between different imaging parameters (e.g., a larger phantom, line source, a point source, or non-uniform patient distribution, and the like).

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
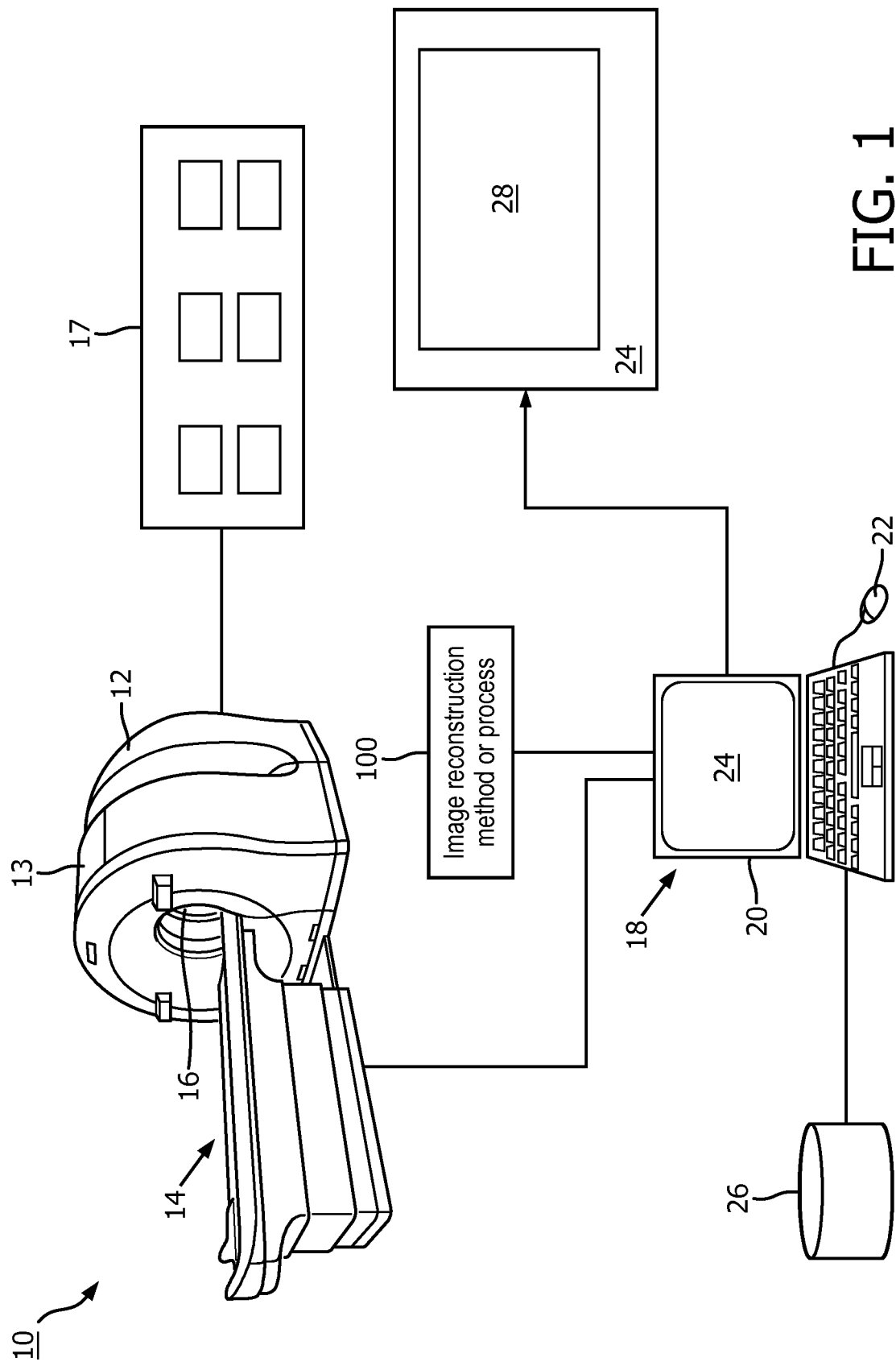
FIG. 1 diagrammatically shows an image reconstruction system according to one aspect.

Dead time is a correction that is of greatest importance at high count rates. In this case, the finite time it takes for the detector to detect a gamma ray (i.e. the "dead time") introduces a non-negligible likelihood that the detector may miss a subsequent gamma ray. Since in PET a line of response (LOR) is detected, one must consider the dead time for each involved detector. By contrast, with some other imaging modalities such as single photon emission computed tomography (SPECT), single photons are detected so that the dead time for a single detector alone is relevant. The probability of detection of a 511 keV gamma ray in PET is computable using the product of the "live time" for each detector, where the live time is the inverse of the dead time. There also can be a dead time component associated with generating the coincidence count along the LOR, apart from the individual detector dead times. This "coincidence" component may, for example, capture the processing time in, for example, a coincidence detection unit (CDU) to identify two temporally coincident detection events and match them as a coincidence count. Again using live time to allow for a product formulation, this is $L_A \times L_B \times L_{coin}$ where $L_A$ and $L_B$ are the live times for the two respective detectors computed in isolation, and $L_{coin}$ is the live time component associated with the LOR coincidence formation.

For the purpose of computing dead time, the available data may be the list mode data, i.e. a listing of timestamped singles events. The embodiments disclosed herein improve on existing dead time computations by taking into account additional factors, leveraging the low-level information available in (or inferable from) the list mode data.

First, the dead time can be larger than that estimated from list mode data alone, because there is additional dead time attributable to multiple detectors being triggered by a single gamma ray. In this case, the "extra" triggers are not recorded as list mode events because the computed energy is not within the "In-Ewindow", i.e., the energy window centered roughly on 511 keV within which events are taken to be 511 keV gamma rays. Yet, these extra triggers contribute to dead time insofar as another gamma ray arriving during the extra trigger may be missed. To account for these extra triggers, a "1-to-N" correction is developed, which employs a relationship of the form N(E) where E is the gamma ray energy and N(E) is the number of triggers statistically occurring for a gamma ray of energy E. In illustrative embodiments, the function N(E) is estimated by Monte Carlo simulation. This can be done as a one-time simulation, and the 1-to-N dead time correction thereafter uses the developed N(E) function.

Second, the dead time can be affected by triggers on low energy gamma rays. These gamma rays fall in a "Below-Ewindow" range which is too low to be recorded as a list mode event but high enough that time is taken to integrate signal to determine the total energy is too low. For example, consider an event with energy 450 keV, when the lower threshold of the Ewindow is 480 keV. In this case, the 450 keV gamma ray triggers the detection sequence, which determines the energy to be 450 keV. As this energy is below the lower threshold (480 keV) for a list mode event, it is discarded. However, this processing contributes to dead time insofar as another gamma ray arriving during the processing of the 450 keV gamma ray detection may be missed. To account for this effect, Monte Carlo simulation is employed to estimate a ratio R of the full window (i.e. In-Ewindow+ Below-Ewindow) counts to the recorded (In-Ewindow) counts of each detector unit.

A third effect can be missed counts due to hardware limitations. For example, some PET systems due to overflow of memory limits when the count rate is extremely high. In some embodiments disclosed herein, additional dead time is provided for accommodating this hardware limitation.

A fourth effect that is optionally accounted for is temperature, which can impact the dead time by shifting the energy photopeak.

In some embodiments disclosed herein, the LOR correction, $L_{coin}$, is determined from phantom measurements. Again, this can be a one-time calibration for one type of detecting system.

Although described herein for PET imaging systems, the disclosed approaches can be employed in conjunction with other imaging modalities, such as computed tomography (CT) imaging systems (operating in a photon-counting mode), single photon emission computed tomography (SPECT) imaging systems, or hybrid systems such as PET/CT or SPECT/CT imaging systems, and the like. In modalities such as SPECT or CT in which the imaging-relevant events are singles (rather than coincidences along LORs as in PET), the disclosed dead time correction factors relating to the coincidence aspect are not incorporated.

As used herein, the term "In-Ewindow" (and variants thereof) refers to photons whose deposited detected energy falls within the acquisition energy window. In other words, events whose energies lie within In-Ewindow are included in the list mode data; whereas, events whose energies lie outside of In-Ewindow are not included in the list mode data.

As used herein, the term "Below-Ewindow" (and variants thereof) refers to photons whose energy falls below the lower threshold of an acquisition energy window but still high enough to trigger a PET detector.

As used herein, the term "Full-Ewindow" (and variants thereof) refers to a combination of in-Ewindow and below-Ewindow.

As used herein, the term "All incidence singles" (and variants thereof) refers to incidence photons whose energy is high enough to trigger the detection process. All incidence singles include both those photons that meet the energy window criteria and also those photons that will be rejected because their energy is below-Ewindow.

As used herein, the term "Detector" (and variants thereof) refers to individual radiation detectors that belong to the same processing unit in terms of dead time. It could be a single detector (crystal) or a group of detectors depending on PET systems. In the case of SPECT, a single detector is suitably a detector aligned with an aperture of a honeycomb collimator or other type of radiation collimator.

As used herein, the term "Live-time" (and variants thereof) refers to a fraction (or equivalently the probability) of the output events out of the input events with some loss in count due to dead-time. For example, the live-time has a theoretical range from 0 to 1. A live-time of 1 would correspond to no dead time. A live-time of 0.8 would indicate that, statistically speaking, the detector is available 80% of the acquisition time and unavailable 20% of the time due to being occupied processing detection triggers. These are merely illustrative examples.

As used herein, the term "Measured singles rate" (and variants thereof) refers to a singles rates output from the detecting system that meet the criteria of energy window, i.e. "in-Ewindow". It could directly come from acquisition if available, or can be derived indirectly from other information such as delayed coincidence count rate. Both are treated as the measured singles rates.

As used herein, the term "System singles rate ($\lambda_{system}$)" (and variants thereof) refers to a sum of the measured singles rates over all detectors. This is to differentiate from the measured singles rates of individual detectors.

As used herein, the term "frame", e.g. "frame of imaging data", denotes an imaging data set acquired over a time interval which is reconstructed to generate a corresponding reconstructed image (i.e. "frame image"). The frame may be acquired at a fixed bed position in the context of multi-bed PET imaging in which each such frame is reconstructed to generate a corresponding frame image with the frame images joined together to produce an axially extended final reconstructed image. Alternatively, in a "single-bed" PET imaging context the frame may be the entire data set acquired with the patient at a single bed position, which is reconstructed to generate the (single) corresponding PET image. The frames may also extend in time, acquired after certain time intervals, leading to dynamic or gated PET.

With reference to FIG. 1, an illustrative medical imaging system 10 is shown. As shown in FIG. 1, the system 10 includes an image acquisition device 12. In one example, the image acquisition device 12 can comprise a PET gantry of a PET/CT imaging system that further includes a computed tomography (CT) gantry 13. In other examples, the image acquisition device 12 can be a standalone PET scanner without a CT component. A patient table (or bed) 14 is arranged to load a patient into an examination region 16 of the PET gantry 12 or CT gantry 13. The PET gantry 12 includes an array of radiation detectors 17 (diagrammatically indicated in FIG. 1; typically, the radiation detectors of the PET gantry 12 are arranged as a series of PET detector rings arranged to span an axial FOV).

The system 10 also includes a computer or workstation or other electronic data processing device 18 with typical components, such as at least one electronic processor 20, at least one user input device (e.g., a mouse, a keyboard, a trackball, and/or the like) 22, and a display device 24. In some embodiments, the display device 24 can be a separate component from the computer 18. The workstation 18 can also include one or more non-transitory storage media 26 (such as a magnetic disk, RAID, or other magnetic storage medium; a solid state drive, flash drive, electronically erasable read-only memory (EEROM) or other electronic memory; an optical disk or other optical storage; various combinations thereof; or so forth). The display device 24 is configured to display a graphical user interface (GUI) 28 including one or more fields to receive a user input from the user input device 22.

The at least one electronic processor 20 is operatively connected with the one or more non-transitory storage media 26 which stores instructions which are readable and executable by the at least one electronic processor 20 to perform disclosed operations including performing an image reconstruction method or process 100. In some examples, the image reconstruction method or process 100 may be performed at least in part by cloud processing.

Figure 2:
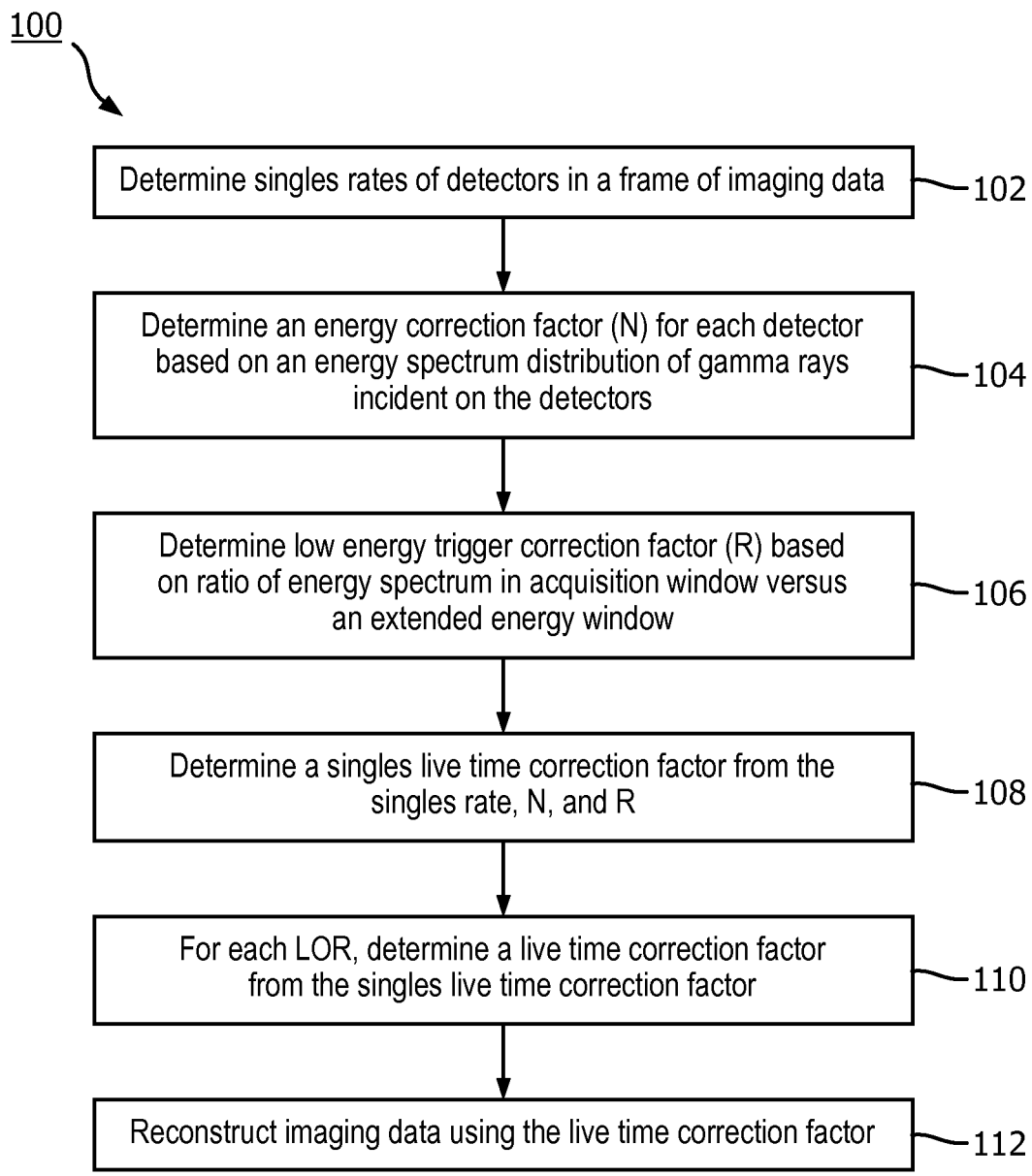
FIG. 2 shows an exemplary flow chart operation of the system of FIG. 1.

With reference to FIG. 2, an illustrative embodiment of the image reconstruction method 100 is diagrammatically shown as a flowchart. To begin the process, the image acquisition device 12 (e.g., the PET imaging device) is configured, or controlled by the at least one electronic processor 20, to acquire PET imaging data detected by the radiation detectors 17. At 102, the at least one electronic processor 20 is programmed to determine singles rates of a plurality of the radiation detectors 17 in a frame of imaging data detected by the radiation detectors. This could be done using hardware for PET systems that log the single rates of individual PET detectors in real time, or may be computed from the acquired list mode PET imaging data, e.g. in one approach the singles rate for each LOR is determined by counting the delayed coincidences (i.e., leveraging the available coincidence detection capability of the PET imaging scanner by using a "delayed" coincidence time window), and the singles rate for a given PET detector is determined based on the delayed coincidences data for LORs involving that PET detector.

At 104, the at least one electronic processor 20 is programmed to determine an energy correction factor ($N_{wgt}$) for each radiation detector 17 based on an energy spectrum distribution of gamma rays incident on the radiation detector during acquisition of the frame of imaging data. To do so, the at least one electronic processor 20 is programmed to determine the value of a function N(E), where N(E) is a statistical count of triggers produced by a gamma ray of energy E. In some embodiments, N(E) is predetermined using Monte Carlo simulation of energy deposition in radiation detectors from a simulated source to obtain an average value of N at each energy E, and the resulting N(E) function is stored as an empirical function, look-up table or the like. The at least one electronic processor 20 is then programmed to determine the energy correction factor ($N_{wgt}$) for each radiation detector by averaging N(E) over the energy spectrum distribution of gamma rays incident on the radiation detector during acquisition of the frame of imaging data. The same function N(E) is used for determining the energy correction factor ($N_{wgt}$) for each radiation detector of the plurality of radiation detectors.

In some embodiments, the at least one electronic processor 20 is programmed to determine the energy spectrum distribution of gamma rays incident on each radiation detector during acquisition of the frame of imaging data using a Monte Carlo simulation operation performed on an initial image reconstructed from the frame of imaging data.

At 106, the at least one electronic processor 20 is programmed to determine a low energy trigger correction factor (R) based on a ratio of the portion of the energy spectrum distribution of gamma rays incident on the radiation detector during acquisition of the frame of imaging data that fall in (i) an acquisition energy window (In-Ewindow) versus (ii) an extended energy window (Full-Ewindow) encompassing the acquisition energy window and a lower trigger energy window (Below-Ewindow). In some examples, the at least one electronic processor 20 is programmed to determine the energy spectrum distribution of gamma rays incident on each radiation detector during acquisition of the frame of imaging data using Monte Carlo simulation performed on an initial image reconstructed from the frame of imaging data. It may be noted that a single Monte Carlo simulation can produce the information for determining the energy spectrum distribution of gamma rays incident on each radiation detector for step 104 and the ratio R per operation 106, and it will be further appreciated that the order of operations 104, 106 may be reversed and/or integrated using a common Monte Carlo simulation processing component.

At 108, the at least one electronic processor 20 is programmed to determine a singles live time correction factor for each radiation detector from the singles rate (from 102), the energy correction factor determined for the radiation detector (from 104), and the low energy trigger correction factor (from 106). In some examples, the singles live time correction factor for each radiation detector is determined further from a dead time factor due to a processing limit of the radiation detector for singles rates higher than a threshold.

At 110, the at least one electronic processor 20 is programmed to, for each LOR of a plurality of LORs connecting pairs of radiation detectors, determining a live time correction factor for the LOR from the determined singles live time correction factors of the pair of radiation detectors connected by the LOR. In some examples, the live time correction factor for each LOR is determined further from a coincidence factor ($L_{coincidence}$) for the LOR that depends on a system singles rate for the frame of imaging data. In further examples, the singles live time correction factor for each radiation detector is determined further from a temperature value of a temperature sensor by taking into account a temperature-dependent energy peak photoshift.

At 112, the at least one electronic processor 20 is programmed to reconstruct the frame of imaging data using the determined LOR live time correction factors. The at least one electronic processor 20 is then programmed to control the display device 24 to display the reconstructed frame image and/or to control the non-transitory storage media 26 to store the clinical image in a suitable database (e.g., a Picture Archiving and Communications System). In the case of multi-station imaging, the processing of FIG. 2 is suitably repeated for each frame and the resulting frame images joined together at operation 112 and displayed as an axially extended reconstructed PET image.

Figure 3:
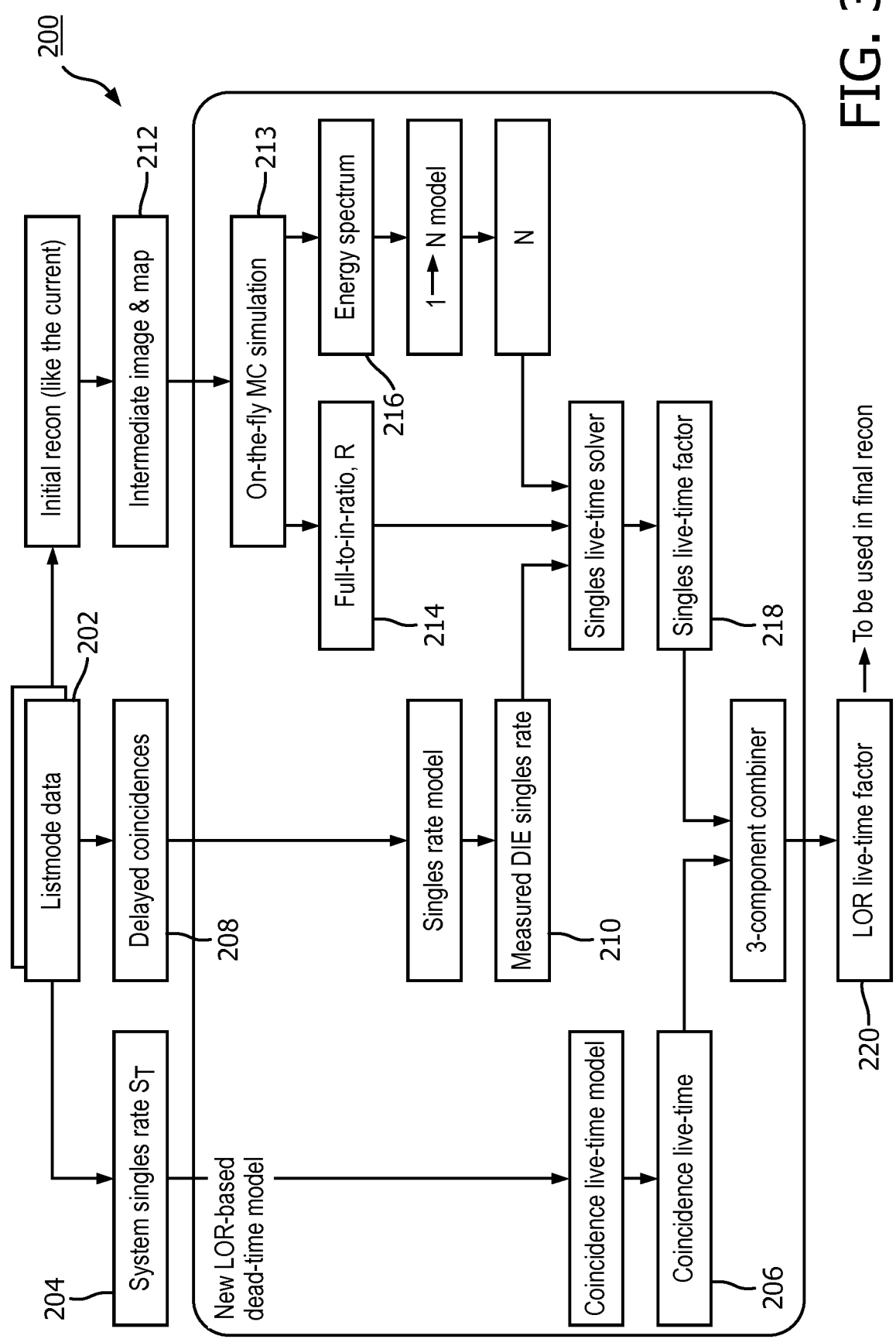
FIG. 3 shows another exemplary flow chart operation of the system of FIG. 1.

With reference to FIG. 3, a more detailed illustrative embodiment of the image reconstruction method 200 is diagrammatically shown as a flowchart. At 202, imaging data to be reconstructed is acquired (e.g., by the image acquisition device 12). At 204, a singles rate $S_T$ of the image acquisition device 12 is determined. At 206, the singles rate $S_T$ is input to a coincidence live-time model to determine a coincidence live-time factor. At 208, delayed coincidences of the imaging data are determined. At 210, the delayed coincidences are input to a singles rate model to determine a measured singles rate of each detector 17. Alternatively, the singles rates of each detector 17 may be available from hardware of the image acquisition device 12 At 212, an initial reconstruction of the imaging data is performed to generate an intermediate reconstructed image and attenuation map. At 213, the intermediate reconstructed image and attenuation map are input to a Monte Carlo simulator to determine a full-to-in-ratio R 214 and an energy spectrum. At 216, the energy spectrum is input to a 1-to-N model where N is a statistical count of triggers produced by a gamma ray of energy to determine an N value. At 218, the measured detector singles rate (from 210), the full-to-in-ratio R (from 214), and the N value (from 216) are input to a single live-time solver to determine a singles live-time correction factor. At 220, the coincidence live time correction factor (from 206) and the singles live-time correction factor (from 218) are input to a three-component combiner to determine a LOR live-time factor to be used in a final image reconstruction operation.

Example

In the following example, illustrative implementations of various operations of the process of FIG. 3 are described in further detail.

As disclosed herein, the live-time factor of each LOR, labeled using its two detectors L (A, B) defining the corresponding LOR, is modeled as a product of 3 components: live-time of singles detection at detector A, live-time of singles detection at B, and live-time of coincidence forming part, as shown in Equation (1).

$$L(A,B) = L_{single}(\lambda_{m,A}, E_A, R_A) \cdot L_{single}(\lambda_{m,B} > E_B > R_B) \cdot L_{coincidence}(\lambda_{system}) \quad (1)$$

In this equation, $\lambda_{m,A}$ and $\lambda_{m,B}$ are the measured singles rates at detectors A and B respectively; $E_A$ and $E_B$ are energy spectrums of incidence singles at detectors A and B respectively; $R_A$ and $R_B$ are the ratios of incidence Full-Ewindow singles rate to incidence In-Ewindow singles A and B respectively; $L_{single}$ is the live-time as a function of $\lambda_m$, E and R, neglecting other factors such as the temperature of detector sensor at this moment. $L_{coincidence}$ is the live-time of coincidence forming part, approximated as a function of the measured system singles rate $\lambda_{system}$.

The singles live-time derived for each LOR is applied to all pixels in the corresponding radiation detectors A. B which detect the event.

To derive $L_{single}$, live-time of singles detection at each detector is typically modeled using non-paralyzable (equation 2), paralyzable (equation 3), or mixed non-paralyzable and paralyzable model (equation 4), depending on the actual system. In these equations, $\tau$ is the effective processing time for each triggered event on average, $\lambda_{events}$ is the rate of total triggered events per detector, and $\theta$ is the portion of the non-paralyzable component in the mixed model. If a system is purely paralyzable, then $\theta$ is 0.

$$L_{non-paral} = \frac{1}{1 + \lambda_{events}\tau} \quad (2)$$

$$L_{paral} = e^{-\lambda_{events}\tau} \quad (3)$$

$$L_{mix} \approx \theta \cdot L_{non-paral} + (1-\theta) \cdot L_{paral} \quad (4)$$

In most studies, $\lambda_{events}\tau$ is relatively small, so equations (2)-(4) can be approximated to (5)-(7) using Taylor Expansion.

$$L_{non-paral} \approx 1 - \lambda_{events}\tau + (\lambda_{events}\tau)^2 \quad (5)$$

$$L_{paral} \approx 1 - \lambda_{events}\tau + \frac{(\lambda_{events}\tau)^2}{2} \quad (6)$$

$$L_{single} = L_{mix} \approx 1 - \lambda_{events}\tau + \left(\frac{1}{2} + \frac{\theta}{2}\right)(\lambda_{events}\tau)^2 \quad (7)$$

Because of 1) the below-Ewindow photon contribution & 2) the 1→N trigger effect, $\lambda_{events}$ can be treated as $$\lambda_{events} = \lambda_{inci,in-Ewin} \cdot R \cdot N + b \quad (8)$$

where $\lambda_{inci,in-Ewin}$ is the incidence In-Ewindow singles rate before dead-time loss, R is the ratio of incidence Full-Ewindow singles rate to incidence In-Ewindow singles rate, N is the factor due to the 1-to-N trigger effect, b is the background rate.

By definition, we have $$L_{single} = \frac{\lambda_{Meas}}{\lambda_{inci,in-Ewin}} \quad (9)$$

where $\lambda_{Meas}$ is the measured singles rate with background rate b already subtracted. Substituting equations (8) and (9) into equation (7), we have Equation 10:

$$\frac{\lambda_{Meas}}{\lambda_{inci,in-Ewin}} = \quad (10)$$

$$1 - (\lambda_{inci,in-Ewin} \cdot R \cdot N + b) \cdot \tau + \frac{(1+\theta)}{2}((\lambda_{inci,in-Ewin} \cdot R \cdot N + b) \cdot \tau)^2$$

This equation can be rearranged into $$\lambda_{Meas} = \lambda_{inci,in-Ewin} \cdot \bigg(1 - (\lambda_{inci,in-Ewin} \cdot R \cdot N + b) \cdot \tau + \quad (11)$$

$$\frac{(1+\theta)}{2}((\lambda_{inci,in-Ewin} \cdot R \cdot N + b) \cdot \tau)^2\bigg)$$

In this equation, $\lambda_{Meas}$, R, N and b can be treated as constant for each detector during a reconstruction. Then Equation (11) is a cubic equation of the unknown variable $\lambda_{inci,in-Ewin}$ and can be further rearranged into $$\frac{(1+\theta)}{2}R^2 \cdot N^2 \cdot \tau^2 \lambda^3_{inci,in-Ewin} + [(1+\theta)R \cdot N \cdot b \cdot \tau^2 - R \cdot N \cdot \tau] \quad (12)$$

$$\lambda^2_{inci,in-Ewin} + \left(1 + \frac{(1+\theta)}{2}b^2 \cdot \tau^2 - b \cdot \tau\right)\lambda_{inci,in-Ewin} - \lambda_{Meas} = 0$$

Solving Equation (12) for each detector gives the answer of the incidence In-Ewindow singles rate, $\lambda_{inci,in-Ewin}$. A cubic equation has 3 roots, either 1 real root and two conjugate complex roots, or 3 real roots. In the scenarios of the dead-time problem, it typically goes to the case of 1 real root and two conjugate complex roots. The only 1 real root is the solution for $\lambda_{inci,in-Ewin}$. Once $\lambda_{inci,in-Ewin}$ has been found, the live-time of singles detection $L_{single}$ can be obtained easily using equation (9) above. In low count rate studies, live-time of singles detection approaching 1.0. In order to avoid bias caused by noise in low count rate studies, live-time can be calculated using Equation (13) in practice.

$$L_{single} = \min\left(\frac{\lambda_{Meas}+b}{\lambda_{inci,in-Ewin}}, 1\right) = \min\left(\frac{\lambda_{Meas\_with\_bkg}}{\lambda_{inci,in-Ewin}}, 1\right) \quad (13)$$

Following this idea, the key point for determining live-time of singles detection is to build the cubic equation (12) for each detector. In the equation, the background rate b and the effective event processing time $\tau$ are typically stable for a given system. They can be fitted from a calibration dynamic study and treated as system level constants for all detectors. The other 3 variables, $\lambda_{Meas}$, R and N, vary with detectors depending on studies and must be figured out as below.

As mentioned earlier, $\lambda_{Meas}$ can be generated directly from detector hardware during acquisition if available, or can be derived from delayed coincidences. Please note $\lambda_{Meas}$ already has the average background rate b subtracted.

Figure 4:
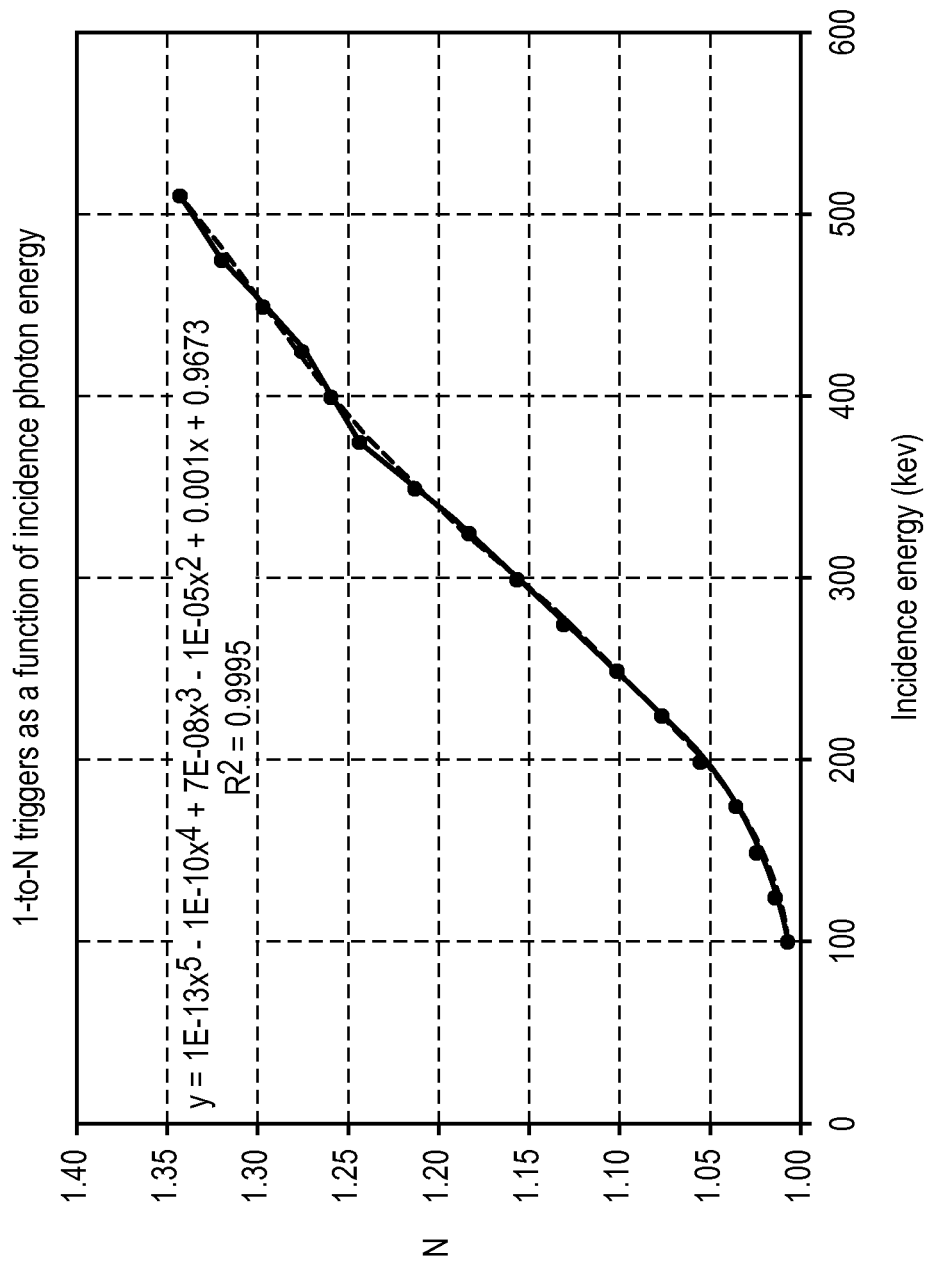
FIG. 4 shows an example of an N(E) relationship for the system of FIG. 1.

To determine N and R, a relationship of N is built as a function of incidence energy, N(E), for a given detector system model. Because a gamma photon hitting a detector can deposit its energy at multiple locations or neighboring detector units, it could trigger one or more (N) events. The average of N depends on detector property and the incidence photon energy. So, for a given PET detector model, perform a series of Monte Carlo simulations of energy deposition in detectors from a point source in air at various emission energy, such as 511, 500, 475, 450, . . . , 100, 50, 25 keV, obtain an average N per primary photon at each emission energy, then from there build a relationship of N as a function of incidence energy, N(E). This is a one-time simulation job for a given detector system model. An example of the N(E) relationship is shown in FIG. 4.

In any reconstruction, an initial reconstruction is performed to generate intermediate image of radioactive distribution.

A quick Monte Carlo simulation on-the-fly is performed using the intermediate image and attenuation map to generate two things for each detector: energy spectrum distribution of incidence γ photons, $H(E_k)$; a ratio of incidence full-Ewindow singles count to incidence in-Ewindow singles count. This is the R value needed for Equation (12).

From the energy spectrum distribution $H(E_k)$, the normalized energy spectrum density function $P(E_k)$ is calculated $$P(E_k) = \frac{H(E_k)}{\sum_{k=1}^{M} H(E_k)} \quad (14)$$

where M is the number of energy spectrum bins.

Using the N(E) relationship from Step 1 and the energy spectrum density function $P(E_k)$ from Step 3, calculate a weighted N value for each detector.

$$N_{wgt} = \frac{\sum_{k=1}^{M} P(E_k) \times N(E_k)}{\sum_{k=1}^{M} P(E_k)} \quad (15)$$

The $N_{wgt}$ is the N value needed for Equation (12).

$\lambda_{Meas}$, R, N, τ and b values are substituted in equation (12) for each detector, solve the cubic equations for the only real root of $\lambda_{inci,in-Ewin}$.

For PET systems that could hit hardware limits at extremely high count rate, such as memory buffer overflow, package drops due to data transfer bandwidth, etc., such data loss cannot be modeled using the typical non-paralyzable, paralyzable or the mixed model. In those situations, apply additional adjustment on $\lambda_{inci,in-Ewin}$ based on empirical models when both the measured in-Ewindow rate $\lambda_{Meas}$ and the derived rate of triggered events ($\lambda_{inci,in-Ewin}\cdot R\cdot N$) are above certain high thresholds.

The live-time of singles detection $L_{single}$ are calculated using equation (9) or equation (13) for very low count rate study.

Figure 5:
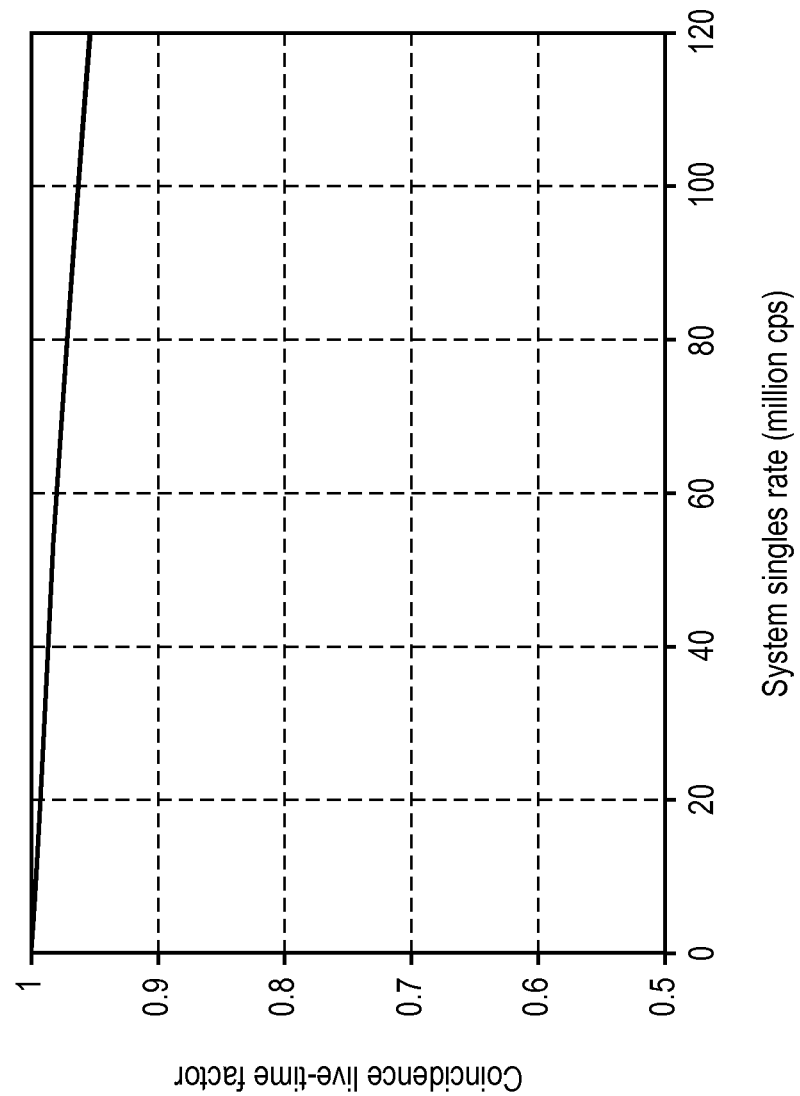
FIG. 5 shows an example of an $L_{coincidence}$ as a function of system singles rate $\lambda_{system}$ of the system of FIG. 1.

To derive $L_{coincidence}$, the live-time of coincidence forming component $L_{coincidence}$ is modeled as a function of the system singles rate $\lambda_{system}$. For a given PET camera model, a response relationship between $L_{coincidence}$ and $\lambda_{system}$ can be derived from a dynamic study of a uniform cylinder phantom by comparing the results with correction for singles detections dead-time only against the known truth. Again, this is a one-time work for a given PET camera model and is applicable to all studies. An example of the $L_{coincidence}$ ($\lambda_{system}$) is shown in FIG. 5.

During reconstruction of any other study, the $L_{coincidence}$ is determined based on the response function from Step 1 above with the actual system singles rate, and apply to all events and LORs.

The above derivations of $L_{single}$ and $L_{coincidence}$ takes into account of the major contributing factors only. Some other factors could also impact live-time. For example, variation in temperature of sensors could lead to changes in sensitivity and shift of photopeak. For further improvement in accuracy, those factors can be included in the model or applied as adjustment if the information is available.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A non-transitory computer-readable medium storing instructions readable and executable by a workstation including at least one electronic processor to perform an image reconstruction method, the method comprising:
   determining singles rates of a plurality of radiation detectors in a frame of imaging data detected by the radiation detectors;
   determining an energy correction factor ($N_{wgt}$) for each radiation detector based on an energy spectrum distribution of gamma rays incident on the radiation detector during acquisition of the frame of imaging data;
   determining a singles live time correction factor for each radiation detector from the singles rate and the energy correction factor determined for the radiation detector;
   for each line of response (LOR) of a plurality of LORs connecting pairs of radiation detectors, determining a live time correction factor for the LOR from the determined singles live time correction factors of the pair of radiation detectors connected by the LOR; and
   reconstructing the frame of imaging data using the determined LOR live time correction factors.

2. The non-transitory computer-readable medium of claim 1, wherein the determining of the energy correction factor ($N_{wgt}$) comprises:
   determining a function N(E) as a function of energy E where N(E) is a statistical count of triggers produced by a gamma ray of energy E; and
   determining the energy correction factor ($N_{wgt}$) for each radiation detector by averaging N(E) over the energy spectrum distribution of gamma rays incident on the radiation detector during acquisition of the frame of imaging data.

3. The non-transitory computer-readable medium of claim 2, further including determining the energy spectrum distribution of gamma rays incident on each radiation detector during acquisition of the frame of imaging data using Monte Carlo simulation performed on an initial image reconstructed from the frame of imaging data.

4. The non-transitory computer-readable medium of claim 2, wherein the same function N(E) is used for determining the energy correction factor ($N_{wgt}$) for each radiation detector of the plurality of radiation detectors.

5. The non-transitory computer-readable medium of claim 2, wherein determining the function N(E) comprises performing Monte Carlo simulation of energy deposition in radiation detectors from a simulated source to obtain an average value of N at each energy E.

6. The non-transitory computer-readable medium of claim 1, wherein the method further comprises:
determining a low energy trigger correction factor (R) based on a ratio of the portion of the energy spectrum distribution of gamma rays incident on the radiation detector during acquisition of the frame of imaging data that fall in (i) an acquisition energy window (In-Ewindow) versus (ii) an extended energy window (Full-Ewindow) encompassing the acquisition energy window and a lower trigger energy window (Below-Ewindow);
wherein the singles live time correction factor for each radiation detector is determined further from the low energy trigger correction factor (R) determined for the radiation detector.

7. The non-transitory computer-readable medium of claim 6, further including determining the energy spectrum distribution of gamma rays incident on each radiation detector during acquisition of the frame of imaging data using Monte Carlo simulation performed on an initial image reconstructed from the frame of imaging data.

8. The non-transitory computer-readable medium of claim 1, wherein the singles live time correction factor for each radiation detector is determined further from a dead time factor due to a processing limit of the radiation detector for singles rates higher than a threshold.

9. The non-transitory computer-readable medium of claim 8, wherein the live time correction factor for each LOR is determined from the determined singles live time correction factors of the pair of radiation detectors connected by the LOR and further from a coincidence factor ($L_{coincidence}$) for the LOR that depends on a system singles rate for the frame of imaging data.

10. An image reconstruction method, comprising:
determining singles rates of a plurality of radiation detectors in a frame of imaging data detected by the radiation detectors;
determining an energy correction factor ($N_{wgt}$) for each radiation detector solely based on an energy spectrum distribution of gamma rays incident on the radiation detector during acquisition of the frame of imaging data;
determining a low energy trigger correction factor (R) based on a ratio of the portion of the energy spectrum distribution of gamma rays incident on the radiation detector during acquisition of the frame of imaging data that fall in (i) an acquisition energy window (In-Ewindow) versus (ii) an extended energy window (Full-Ewindow) encompassing the acquisition energy window and a lower trigger energy window (Below-Ewindow);
determining a singles live time correction factor for each radiation detector from the singles rate, the energy correction factor determined for the radiation detector, and the low energy trigger correction factor;
for each line of response (LOR) of a plurality of LORs connecting pairs of radiation detectors, determining a live time correction factor for the LOR from the determined singles live time correction factors of the pair of radiation detectors connected by the LOR;
reconstructing the frame of imaging data using the determined LOR live time correction factors; and
at least one of displaying the reconstructed frame of imaging data and storing the reconstructed frame of imaging data.

11. The method of claim 10, wherein the determining of the energy correction factor ($N_{wgt}$) comprises:
determining a function N(E) where N(E) is a statistical count of triggers produced by a gamma ray of energy E; and
determining the energy correction factor ($N_{wgt}$) for each radiation detector by averaging N(E) over the energy spectrum distribution of gamma rays incident on the radiation detector during acquisition of the frame of imaging data.

12. The method of claim 11, further including determining the energy spectrum distribution of gamma rays incident on each radiation detector during acquisition of the frame of imaging data using Monte Carlo simulation performed on an initial image reconstructed from the frame of imaging data.

13. The method of claim 11, wherein the same function N(E) is used for determining the energy correction factor ($N_{wgt}$) for each radiation detector of the plurality of radiation detectors.

14. The method of claim 11, wherein determining the function N(E) comprises performing Monte Carlo simulation of energy deposition in radiation detectors from a simulated source to obtain an average value of N at each energy E.

15. The method of claim 10, further including determining the energy spectrum distribution of gamma rays incident on each radiation detector during acquisition of the frame of imaging data using Monte Carlo simulation performed on an initial image reconstructed from the frame of imaging data.

16. The method of claim 10, wherein the live time correction factor for each LOR is determined from the determined singles live time correction factors of the pair of radiation detectors connected by the LOR and further from a coincidence factor ($L_{coincidence}$) for the LOR that depends on a system singles rate for the frame of imaging data.

17. An imaging system, comprising:
an image acquisition device comprising a plurality of radiation detectors; and
at least one electronic processor programmed to:
determine singles rates of a plurality of radiation detectors in a frame of imaging data detected by the radiation detectors;
determine a low energy trigger correction factor (R) based on a ratio of the portion of the energy spectrum distribution of gamma rays incident on the radiation detector during acquisition of the frame of imaging data that fall in (i) an acquisition energy window (In-Ewindow) versus (ii) an extended energy window (Full-Ewindow) encompassing the acquisition energy window and a lower trigger energy window (Below-Ewindow), the low energy trigger correction factor (R) being determined independent of the determined singles are of the plurality of radiation detectors;
determine a singles live time correction factor for each radiation detector from the singles rate and the low energy trigger correction factor (R);
for each line of response (LOR) of a plurality of LORs connecting pairs of radiation detectors, determine a live time correction factor for the LOR from the determined singles live time correction factors of the pair of radiation detectors connected by the LOR; and
reconstruct the frame of imaging data using the determined LOR live time correction factors.

18. The system of claim 17, wherein the at least one electronic processor is programmed to:

determine an energy correction factor ($N_{wgt}$) for each radiation detector based on an energy spectrum distribution of gamma rays incident on the radiation detector during acquisition of the frame of imaging data; and determine the singles live time correction factor for each radiation detector is further from the energy correction factor determined for the radiation detector.

19. The system of claim 18, wherein the at least one electronic processor is programmed to:

determine a function N(E) where N(E) is a statistical count of triggers produced by a gamma ray of energy E; and determine the energy correction factor ($N_{wgt}$) for each radiation detector by averaging N(E) over the energy spectrum distribution of gamma rays incident on the radiation detector during acquisition of the frame of imaging data.

20. The system of claim 19, wherein the at least one electronic processor is programmed to:

determine the energy spectrum distribution of gamma rays incident on each radiation detector during acquisition of the frame of imaging data using Monte Carlo simulation performed on an initial image reconstructed from the frame of imaging data.

* * * * *